United States Patent
Holmes

(10) Patent No.: US 8,267,859 B2
(45) Date of Patent: Sep. 18, 2012

(54) SPREADER INSERT FOR A RETRACTOR SYSTEM

(75) Inventor: Russell P. Holmes, Dover, MA (US)

(73) Assignee: Holmed Corporation, South Easton, MA (US)

( * ) Notice: Subject to any disclaimer, the term of this patent is extended or adjusted under 35 U.S.C. 154(b) by 462 days.

(21) Appl. No.: 11/525,450

(22) Filed: Sep. 22, 2006

(65) Prior Publication Data

US 2007/0073112 A1    Mar. 29, 2007

Related U.S. Application Data

(60) Provisional application No. 60/721,426, filed on Sep. 28, 2005.

(51) Int. Cl.
*A61B 1/32* (2006.01)

(52) U.S. Cl. .......................................... 600/213

(58) Field of Classification Search .......... 600/201–246; 606/198
See application file for complete search history.

(56) References Cited

U.S. PATENT DOCUMENTS

| | | | |
|---|---|---|---|
| 2,083,573 A | | 4/1936 | Morgan |
| 2,623,517 A | * | 12/1952 | Barlow et al. ............... 600/233 |
| 3,841,318 A | * | 10/1974 | Olson ......................... 600/220 |
| 4,432,351 A | * | 2/1984 | Hoary ......................... 600/220 |
| 5,125,396 A | * | 6/1992 | Ray ............................ 600/208 |
| 5,505,690 A | * | 4/1996 | Patton et al. ................ 600/210 |
| 5,944,658 A | | 8/1999 | Koros et al. |
| 6,083,154 A | | 7/2000 | Liu et al. |
| 7,374,534 B2 | * | 5/2008 | Dalton ........................ 600/222 |
| 2004/0176665 A1 | * | 9/2004 | Branch et al. .............. 600/210 |
| 2005/0215866 A1 | * | 9/2005 | Kim ............................ 600/233 |
| 2005/0277812 A1 | * | 12/2005 | Myles ........................ 600/231 |

FOREIGN PATENT DOCUMENTS

FR    2865924 A1    9/2004

OTHER PUBLICATIONS

PCT Invitation to Pay Additional Fees and Partial International Search, PCT/US2006/037367, International Filing Date: Sep. 25, 2006, Mailing Date: Mar. 3, 2007.

* cited by examiner

*Primary Examiner* — Eduardo C Robert
*Assistant Examiner* — Steven Cotroneo
(74) *Attorney, Agent, or Firm* — Cesari and McKenna, LLP

(57) ABSTRACT

A spreader insert for use with a surgical retractor is provided. The spreader insert includes a circular head with two or more downwardly extending blades. One end of each blade of the insert is rotatably fastened to the head of the insert, such that each blade can be tilted inwardly or extended outwardly from a central axis of the device. Suitable fasteners are provided to rotate the blades from a closed position in which the distal ends of the blades are almost touching each other in order to improve ease of introduction into the surgical field. In an open position, the blades rotate outwardly to hold body tissue in place. Alternatively, the entire spreader insert is machined from a hardenable steel tube, the blades of which are formed so that, when released, they spring outwardly to an open position.

13 Claims, 7 Drawing Sheets

CLOSED POSITION

OPEN POSITION

OPEN POSITION

SPREADER INSERT FOR A RETRACTOR SYSTEM

CROSS-REFERENCE TO RELATED APPLICATION

The present application claims the benefit of U.S. Provisional Patent Application Ser. No. 60/721,426, which was filed on Sep. 28, 2005, by Russell P. Holmes for a SPREADER INSERT FOR A RETRACTOR SYSTEM, which is hereby incorporated by reference.

BACKGROUND OF THE INVENTION

1. Field of the Invention

This invention relates to surgical instrumentation, and more particularly, to instrumentation for use in spinal surgery and other types of surgical procedures.

2. Background Information

Surgery on the spine is becoming more prevalent as better processes for performing many different types of spinal surgery are developed for procedures such as disk repair, vertebral fracture repair, correcting the effects of osteoporosis, bone grafts, tumor removal, scoliosis, and the like.

Many different types of surgical instruments are used both to clear the field for the surgeon and to allow the spine surgeon access to the region of interest. In a number of cases, a surgeon needs to work at two different levels of the spine. Retractors are typically used to retract muscle and connective tissue in order to provide the surgeon clear visibility of the area of the surgical field. Retractors are designed to be large enough to provide the strength needed to spread or retract muscle and connective tissue without bending, particularly when the surgeon is operating on the spine. However, such strong instruments are usually of a greater thickness and this may act to obstruct the view of the surgeon.

Additionally, another problem arises with respect to ring-type surgical retractors in that they retract the muscle and tissue in a circular region which does not always provide enough visibility in certain procedures. For example, many ring-type retractors operate in a direction of the spine to the stomach. Such retractors include arcuate blades that extend in an arch approximately 40 degrees to 60 degrees around an inner ring thus providing a cylindrical opening along a common axis extending from spine to stomach. However, this does not always provide enough visibility and can still result in muscle and tissue encroaching back into the surgical field during the surgical procedure.

There remains a need, therefore, for an insert in a surgical retractor of the ring type configuration which provides further retraction and thus additional visibility.

SUMMARY OF THE INVENTION

These and other disadvantages of the prior art are provided by the present invention which is a spreader insert for a surgical retractor for use in retracting tissue during a surgical procedure. The spreader insert includes a circular head with two or more downwardly extending blades. One end of each blade of the insert is rotatably fastened to the head of the insert, such that each blade can be tilted inwardly or extended outwardly from a central axis of the device. In accordance with one aspect of the invention, suitable fasteners are provided to rotate the blades from a closed position in which the distal ends of the blades are almost touching each other in order to improve ease of introduction into the surgical field. The fasteners also allow the blades to be rotated outwardly to an open position to provide additional retraction needed by the surgeon. In accordance with another aspect of the invention, the spreader insert is machined from a hardenable steel tube, the blades of which are formed so that they tend to spring outwardly unless they are held in place. More specifically, the blades are held inward in a closed position during insertion of the spreader insert into a body cavity, and then after insertion, the blades are released and thus spring outwardly to an open position, without the need to actuate a screw or other device. The spreader insert of the present invention is mounted into a stabilizing device, which may be a ring-type retractor base to form a retractor assembly.

In use, the whole retractor assembly is introduced into the surgical field. Upon introduction, the initial configuration of the spreader insert is the closed position in that the downwardly extending blades of the spreader insert are tilted inwardly. Thus, the distal ends of each blade are almost touching one another to allow ease of introduction. Once inserted at the desired location, the base retractor forms a circular field of visibility. The surgeon then causes the blades to be expanded outwardly by operating the fasteners of the spreader insert of the first embodiment of the invention to rotate the blades outwardly, or by releasing the blades in the spring-out embodiment. In either case, the expanded blades act to spread the muscle and tissue further to provide retraction beyond the ring formed by the base retractor. The additional expansion of the opening provided by the base retractor is extended in the direction of head-to-toe of the patient, as opposed to spine to stomach. Thus, by using the insert with a ring-type retractor, the "creep' of muscle or other tissue into the surgical field is reduces thus leaving a larger and more secure surgical area to be exposed for surgical access.

BRIEF DESCRIPTION OF THE DRAWINGS

The invention description below refers to the accompanying drawings, of which.

DETAILED DESCRIPTION OF AN ILLUSTRATIVE EMBODIMENT

Figure 1:
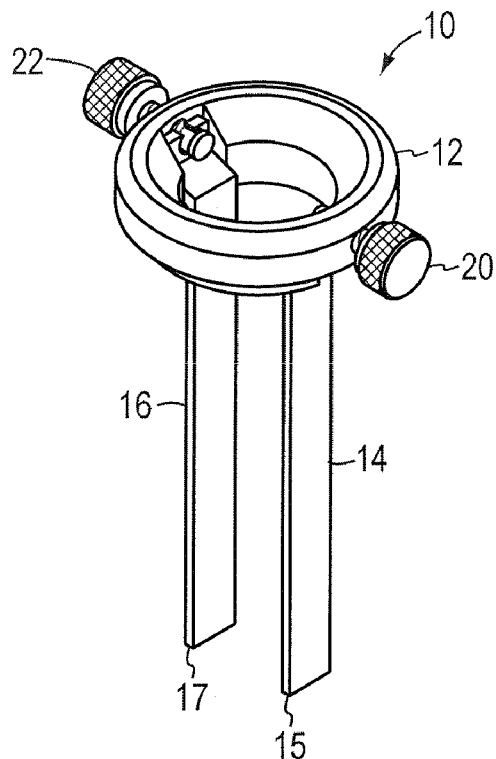
FIG. 1 is an isometric illustration of the spreader insert of the present invention in a closed position.
Figure 2:
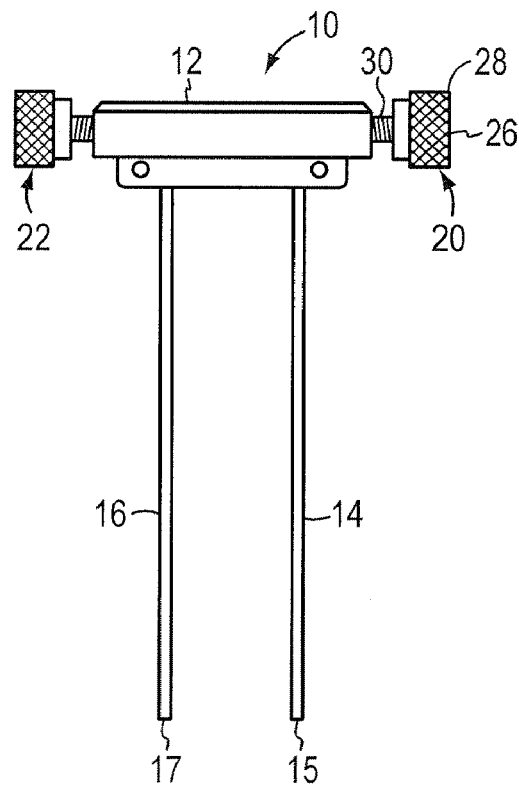
FIG. 2 is a side elevation of the spreader insert of the present invention in a closed position.

FIG. 1 is an isometric illustration of the spreader insert 10 of the present invention. The spreader insert 10 comprises a head portion 12 and a first blade 14 and a second blade 16. It is noted that the illustrative embodiment of FIG. 1 includes two blades, 14 and 16. However, it should be understood that the spreader insert 10 can be readily adapted to include more than two downwardly extending blades, such as those illustrated in FIG. 1, while remaining within the scope of the present invention. Blades 14 and 16 are coupled to the head 12 by means of fasteners 20 and 22. These are also visible in FIG. 2.

Figure 3:
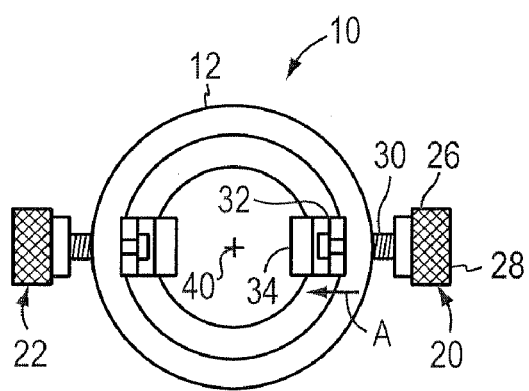
FIG. 3 is a top plan view of the head of the spreader insert of the present invention illustrating the fasteners for rotating the blades of the insert.

FIG. 3 is a top plan view of the insert 10 of the present invention illustrating the fasteners 20 and 22 in greater detail. More specifically, fastener 20 includes a screw 26 having a head 28 and a threaded shaft 30. An end 32 of the threaded shaft 30 is coupled to the tip 34 of the blade 14. When the screw head 28 is rotated in a first direction, the tip 34 is pushed inwardly towards the central axis 40 of the device. This motion in the direction of the arrow A, adjusts the tip 34 of the blade 14, in towards the central axis of the device to thus cause the distal end 15 of the blade 14 to rotate outwardly. When the head 28 is manipulated in an opposite direction, the shaft 30 draws the blade tip 34 in towards the head 28 to thus rotate the distal end 15 of the blade 14 inwardly towards the central axis of the device.

Figure 4:
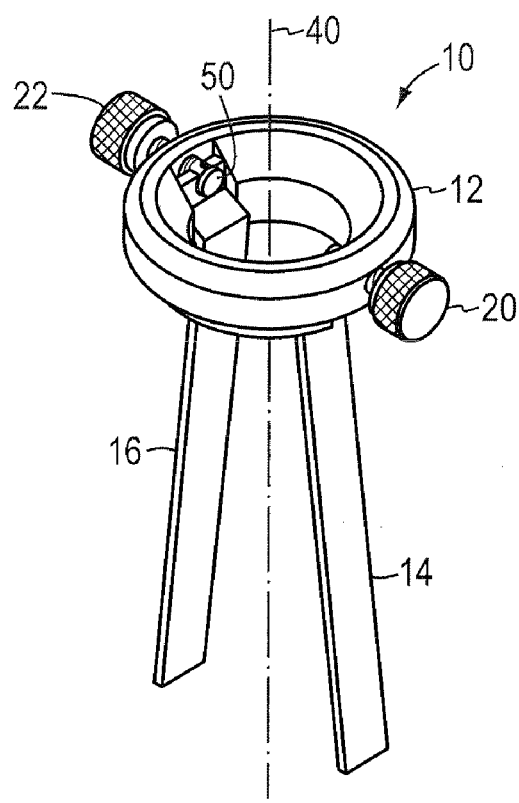
FIG. 4 is an isometric illustration of the spreader insert of the present invention in an open position.
Figure 5:
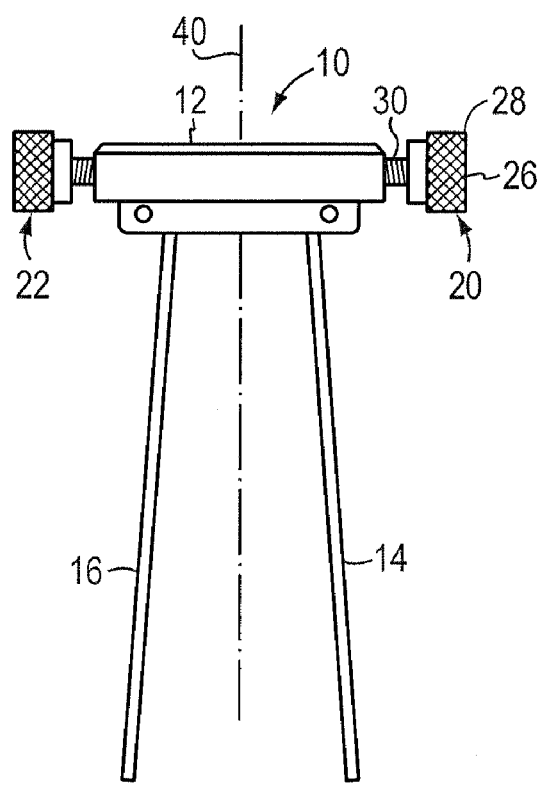
FIG. 5 is a side section of the device of FIG. 4.

FIG. 4 is an isometric illustration of the insert 10 of the present invention illustrated in the open position in which downwardly extending blades 14 and 16 are rotated outwardly away from the central axis 40 of the device. This is also illustrated in the side section of FIG. 5. The open position extends the visibility of the surgical field and assists the surgeon in working on two different levels. This is especially useful in micro surgery in the lumbar region.

Figure 6:
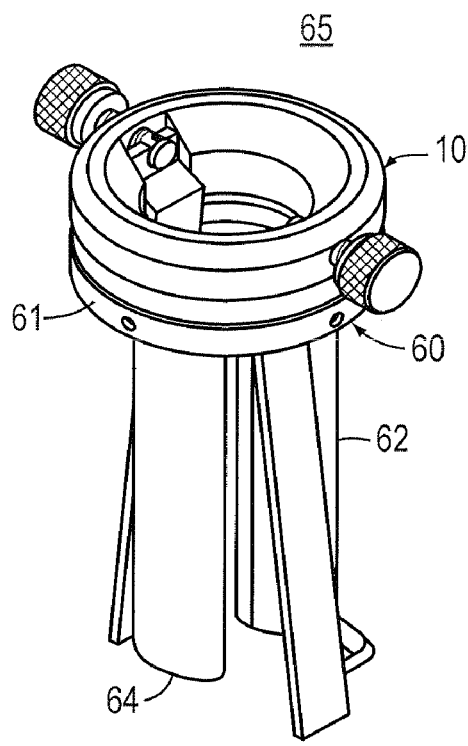
FIG. 6 is an isometric illustration of a spreader insert of the present invention utilized with a ring-type surgical retractor to form an illustrative embodiment of a retractor assembly.
Figure 7:
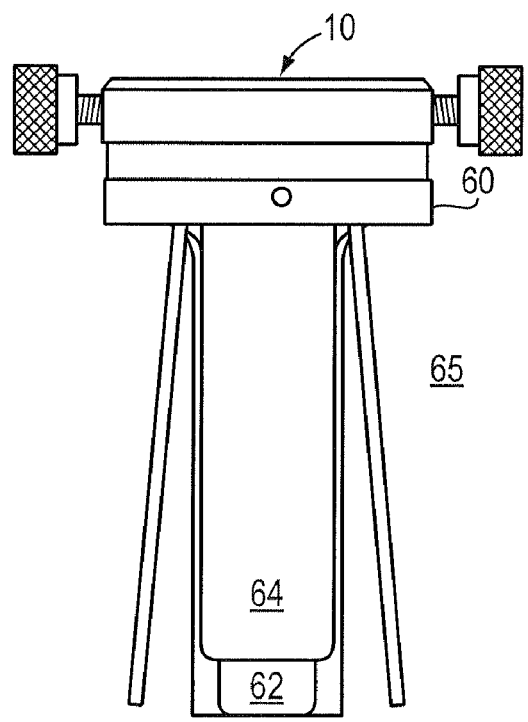
FIG. 7 is a side elevation of the retractor assembly of FIG. 6 in an open position.
Figure 8:
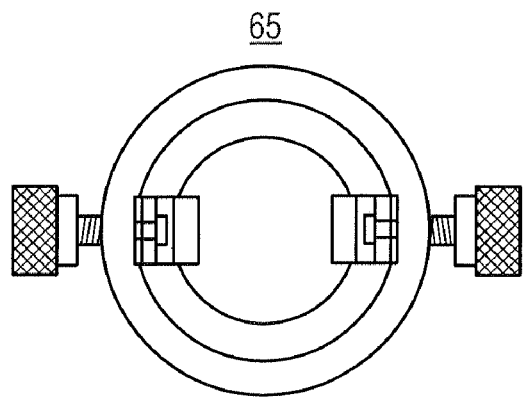
FIG. 8 is a top plan view of the retractor assembly of FIG. 6.

FIGS. 6, 7 and 8 are isometric illustrations of a retractor assembly 65 that includes the spreader insert 10 of the present invention as assembled within a ring-type retractor. More specifically, the insert 10 is received within the retractor base 60. The retractor base 60 has an outer ring, 61 having an arm 62 mounted thereon and an inner ring (not shown) upon which an arm 64 is disposed. After insertion, the rings can rotated to provide a cylindrical type retraction of the area.

Figure 9:
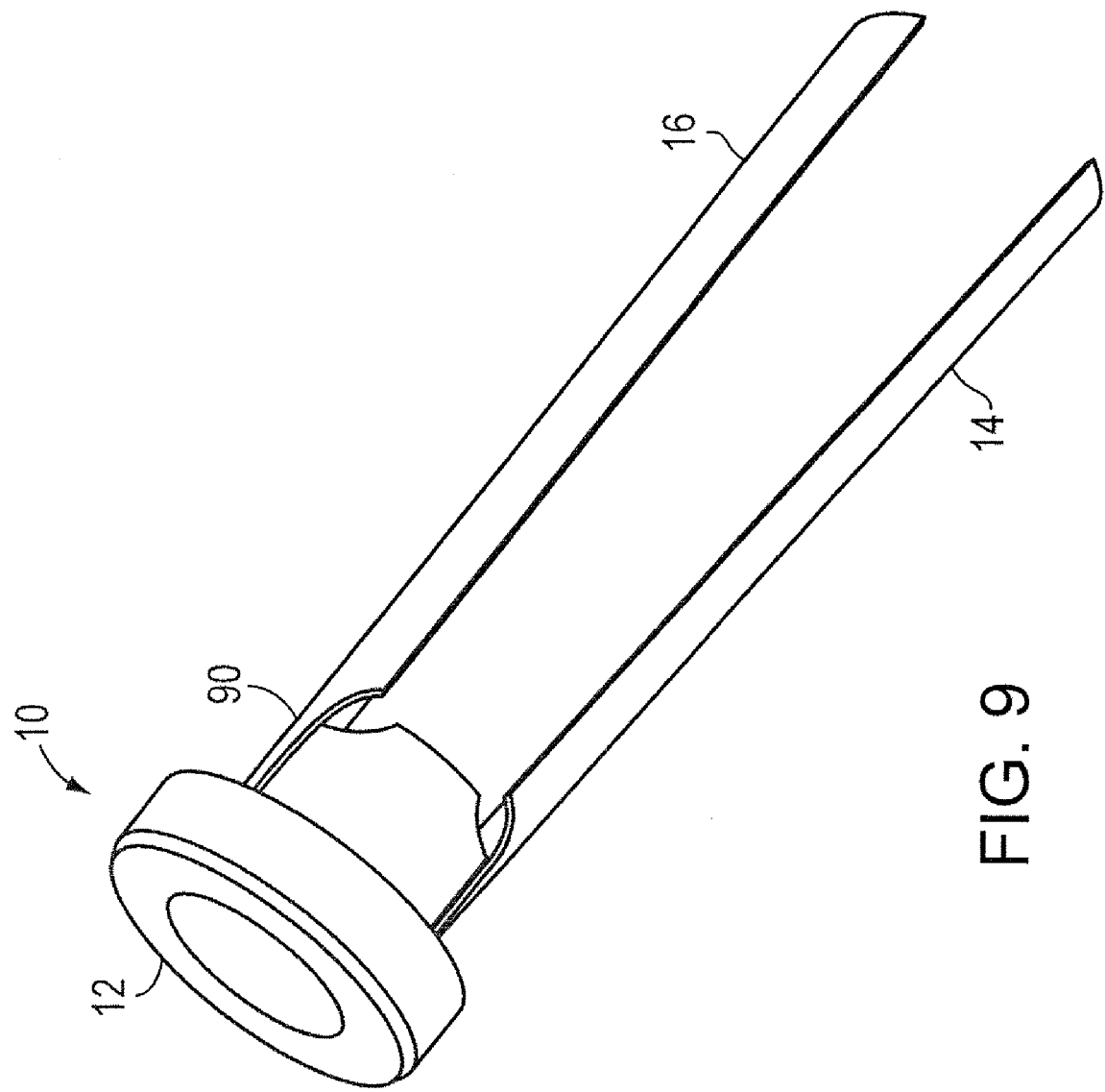
FIG. 9 is a side elevation of an illustrative embodiment of the spreader insert of the present invention in which the blades are formed from hardenable steel and spring outwardly when released.
Figure 10:
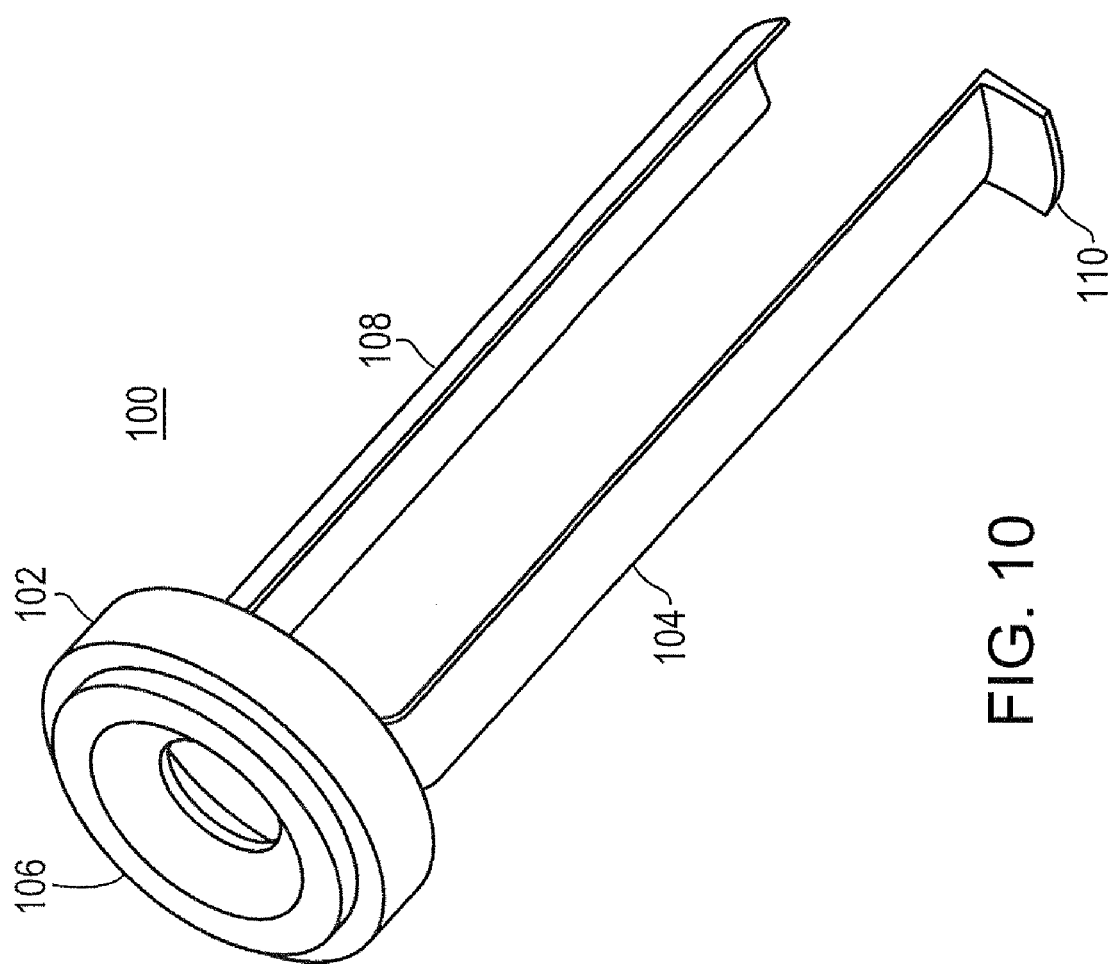
FIG. 10 is an isometric illustration of an embodiment of a retractor base in accordance with an illustrative embodiment of the present invention.

It should be understood, that many other types of couplings and fasteners can be used to provide the rotation upon the blades 14 and 16 and to adjust the spreader insert 10 between the closed and open positions, as will be understood by those skilled in the art. In accordance with a further aspect of the invention, the spreader insert can be formed of a hardenable steel such that the blades of which are formed so that they tend to spring outwardly unless they are held in place. More specifically, as illustrated in FIG. 9, a spreader insert 10 has a head portion 12 and blades 14 and 16. In this embodiment the blades 14 and 16 are formed of a hardenable steel body 90 such that the blades tend to urge outwardly unless they are held inward in a closed position. Thus, during insertion of the spreader insert 10 into a body cavity, the blades are crimped by the retractor base 100 as shown in FIG. 10. The retractor base 100 has a head 102, which has a stationary downwardly extending arm 104. A second cylindrical portion 106 is received within the head 102, and this second portion has its own downwardly extending stationary arm 108.

Notably, the arm 104 has a flange 110 thereupon which acts to steady the retractor assembly and to anchor it in place in the body cavity.

Figure 11:
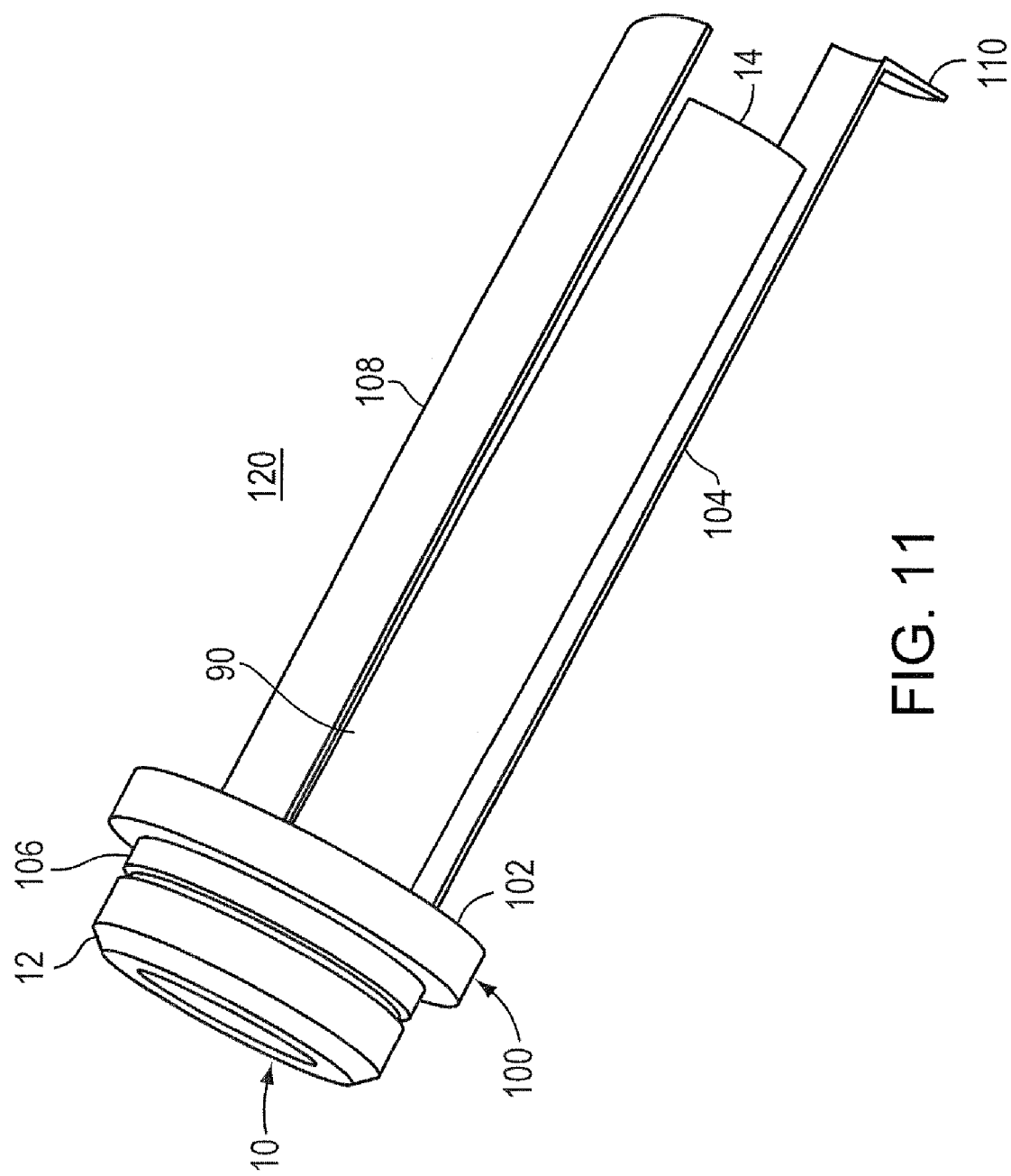
FIG. 11 is a side elevation of an illustrative embodiment of the retractor assembly of the present invention that incorporates the components of FIGS. 9 and 10.
Figure 12:
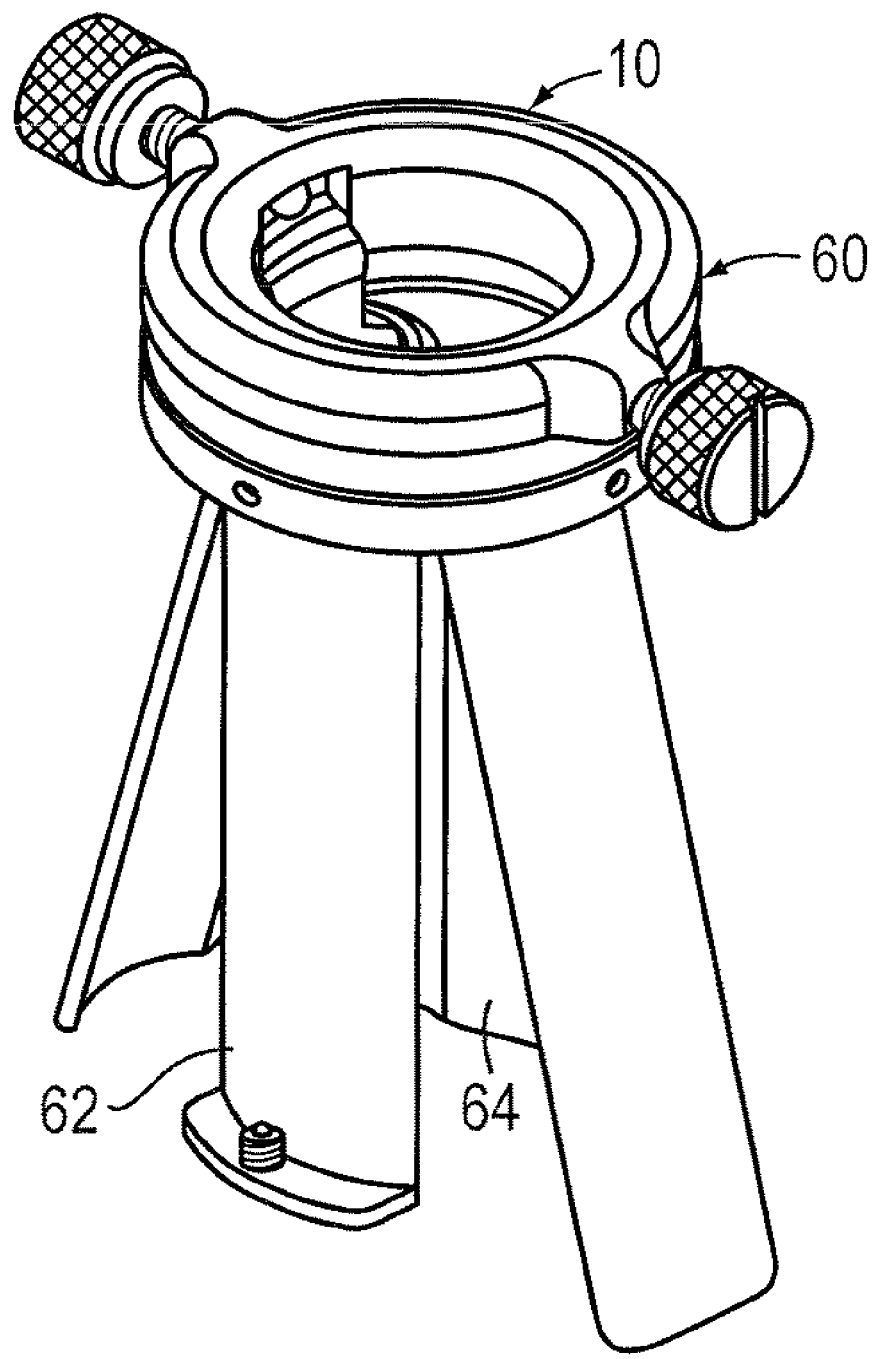
FIG. 12 is the spreader insert of FIG. 6 also having a flange and screw assembly disposed on one arm thereof.

A retractor assembly in accordance with the invention which incorporates the components of FIGS. 9 and 10 is illustrated in FIG. 11. In FIG. 11, the retractor assembly 120 includes the spreader insert 10, which is received within the head 102 of the retractor base 100. The blades 14 and 16 of the spreader insert 10 are spaced 180 degrees from one another and are located on their own head assembly so that, in a closed position, they can be held in place underneath the respective adjacent stationary arm 104, 108 of the retractor base 100. Then, the spreader insert 10 can be rotated about 90 degrees to thus allows the blades 14 and 16 to expand outwardly while the stationary arms 104, 106 remain in place.

In operation, the entire retractor assembly 120 is inserted at the desired location in the body of a patient requiring surgery. During insertion, the blades 14,16 are held in place by the stationary arms 104, 108 of the retractor base 100. Then, when the whole assembly is at the desired location, the spreader insert 10 is rotated to allow the spring out blades 14, 16 to be released and thus spring outwardly to an open position, without the need to actuate a screw or other device.

The entire device may be constructed of surgical steel, or alternatively, various components of the device may be constructed of one or more materials selected from the group consisting of stainless steel, titanium and plastics. It should be understood that the spreader insert and the retractor assembly of the present invention reduce creep of muscle and other tissue and thus provide additional visibility and stability for a surgeon working on the spinal region using outwardly extending blades that allow for further extension of the surgical field beyond that provided when using with a ring-type surgical retractor alone.

It should also be understood that the forgoing description has been directed to a particular embodiments of the invention. It should be apparent, however, that other variations and modifications may be made to the described embodiments with the attainment of some or all of their advantages. Therefore, those skilled in the art should recognize that changes may be made in form and detail without departing from the spirit and scope of the invention.

What is claimed is:

1. A retractor assembly for use in a surgical procedure, comprising:
   a. a retractor base having a generally cylindrical head portion and two or more downwardly extending stationary arms; and
   b. a spreader insert having a head portion and two or more downwardly extending blades rigidly attached to said head portion, said two or more downwardly extending blades of said spreader insert being machined of hardenable steel and formed such that distal ends of said blades tend to spring outwardly from a central axis of said head portion unless held in place, said spreader insert being received within said retractor base and configured such that said blades of said spreader insert, when in a closed position, are maintained adjacent and beneath said arms of said retractor base, and configured such that when the spreader insert is adjusted to an open position, said distal ends of said blades spring outwardly to hold body tissue in a desired location.

2. The retractor assembly as defined in claim 1 further comprising said retractor base having two downwardly extending arms that are disposed about 180 degrees from one another.

3. The retractor assembly as defined in claim 1 further comprising said spreader insert having two downwardly extending blades that are each held adjacent to and beneath the arms of said retractor base, when in the closed position, and said spreader insert, when turned, to release said blades from said arms, to allow said distal ends of said blades to spring outwardly to said open position.

4. The retractor assembly as defined in claim 1 further comprising at least one of said arms of said retractor base having a flange disposed at a distal end thereof.

5. The retractor assembly as defined in claim 1 wherein one or more portions of said retractor assembly are comprised of materials selected from the group consisting of stainless steel, titanium and plastics.

6. A retractor assembly for use in a surgical procedure, comprising:
   a retractor base having a generally cylindrical head portion, said generally cylindrical head portion including an outer ring having a first downwardly extending arm mounted thereon and an inner ring having a second downwardly extending arm mounted thereon, the outer ring having the first downwardly extending arm and inner ring having the second downwardly extending arm rotatable with respect to each other; and
   a spreader insert configured to be received within said retractor base, said spreader insert including
   a generally cylindrical head portion,
   two or more downwardly extending rotatable blades coupled to said head portion of said spreader insert, each blade machined as a single integral rigid component having a blade tip at one end and a distal end at an opposing end, each blade configured to rotate such that the distal end of said blade travels inwardly from parallel to a central axis of said head portion of said spreader insert for introduction into a body cavity, and to rotate such that the distal end of said blade travels outwardly from parallel to said central axis of said head portion of said spreader insert to hold bodily tissue in a predetermined location when in the body cavity, each blade to rotate independently with respect to any other blade, and
   a screw assembly coupled to said head portion of said spreader insert and to a corresponding blade, the screw assembly including a rotatable screw with portions that contact both said blade tip of said corresponding blade and said head portion of said spreader insert such that rotation of said screw in a first direction draws said blade tip towards said head portion of said spreader insert and thus causes said distal end of said blade to extend inwardly toward said central axis of said head portion of said spreader insert to a closed position, and rotation of said screw in a second direction urges said blade tip away from said head portion of said spreader insert and thus causes said distal end of said blade to extend outwardly from said central axis of said head portion of said spreader insert to an open position, the closed position and the open position being at the full extent of said blade's range of motion.

7. The retractor assembly as defined in claim 6 wherein the two or more rotatable blades are two rotatable blades disposed on said head portion of said spreader insert opposite from one another.

8. The retractor assembly as defined in claim 6 wherein at least one of said downwardly extending arms of said retractor base has a flange disposed at a distal end thereof.

9. The retractor assembly as defined in claim 6 wherein said spreader insert is constructed from stainless steel.

10. A retractor assembly for use in a surgical procedure, comprising:
    a spreader insert including
    a generally cylindrical head portion, and
    two or more downwardly extending blades rigidly attached to said generally cylindrical head portion, said two or more downwardly extending blades being machined of hardenable steel and formed such that distal ends of said blades tend to spring outwardly from a central axis of said head portion unless held in place in a closed position, said two or more downwardly extending blades configured such that, when the spreader insert is adjusted to an open position, said distal ends of said blades spring outwardly without need to actuate a screw or other device to urge them outwardly; and
    a retractor base having a retractor base head portion and two or more stationary, downwardly extending arms coupled to said retractor base head portion, said retractor base head portion to receive said head portion of said spreader insert, each of said blades held adjacent to and beneath a respective one of said arms of said retractor base when the blades are in the closed position, and said spreader insert, when adjusted to release said blades from said arms, to allow said distal ends of said blades to spring outwardly to said open position.

11. The retractor assembly as defined in claim 10 wherein the two or more blades are two blades disposed on said head portion opposite from one another.

12. The retractor assembly as defined in claim 10 wherein at least one of said arms of said retractor base has a flange disposed at a distal end thereof.

13. The retractor assembly as defined in claim 10 wherein said spreader insert is constructed from stainless steel.

* * * * *